(12) United States Patent
Saito et al.

(10) Patent No.: US 8,860,794 B2
(45) Date of Patent: Oct. 14, 2014

(54) ENDOSCOPE SYSTEM

(71) Applicant: Olympus Medical Systems Corp., Tokyo (JP)

(72) Inventors: Saeri Saito, Sagamihara (JP); Jun Konishi, Hachioji (JP); Hiroyuki Usami, Nishitokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/937,341

(22) Filed: Jul. 9, 2013

(65) Prior Publication Data

US 2014/0015947 A1    Jan. 16, 2014

Related U.S. Application Data

(63) Continuation of application No. PCT/JP2012/083356, filed on Dec. 21, 2012.

(30) Foreign Application Priority Data

Mar. 6, 2012    (JP) .................................. 2012-049781

(51) Int. Cl.
  *A61B 1/00*    (2006.01)
  *A61B 1/045*    (2006.01)
  *G02B 23/24*    (2006.01)
(52) U.S. Cl.
  CPC ........... *A61B 1/0002* (2013.01); *A61B 1/00059* (2013.01); *A61B 1/045* (2013.01); *A61B 1/00057* (2013.01); *G02B 23/2476* (2013.01)
  USPC ......................................................... 348/74
(58) Field of Classification Search
  CPC ........... G02B 23/2476; A61B 1/00057; A61B 1/0002; A61B 1/045; A61B 1/00059
  USPC ......................................................... 348/74
  See application file for complete search history.

(56) References Cited

U.S. PATENT DOCUMENTS

2006/0142641 A1    6/2006    Sato
2006/0178565 A1    8/2006    Matsui et al.

FOREIGN PATENT DOCUMENTS

| JP | 2003-19105 A | 1/2003 |
|---|---|---|
| JP | 2006-175215 A | 7/2006 |
| JP | 2006-212335 A | 8/2006 |
| JP | 2007-208926 A | 8/2007 |
| JP | 2007-279238 A | 10/2007 |

OTHER PUBLICATIONS

International Search Report dated Jan. 22, 2013 from related International PCT Application PCT/JP2012/083356.

*Primary Examiner* — Andy Rao
*Assistant Examiner* — Nguyen Truong
(74) *Attorney, Agent, or Firm* — Scully, Scott, Murphy & Presser, P.C.

(57) ABSTRACT

An endoscope system includes an imaging apparatus that outputs, as image information, an electrical signal photoelectrically converted from a plurality of pixels, outside the imaging apparatus, and a processing apparatus that is connected to the imaging apparatus so as to bi-directionally communicate with the imaging apparatus. The imaging apparatus includes a first recording unit that records identification information for identifying the imaging apparatus. The processing apparatus includes a second recording unit that records correction information for correcting characteristics of the imaging apparatus in association with the identification information, and a control unit that acquires, from the second recording unit, the correction information corresponding to the identification information received from the imaging apparatus and transmits the correction information to the imaging apparatus.

3 Claims, 8 Drawing Sheets

ENDOSCOPE SYSTEM

CROSS-REFERENCE TO RELATED APPLICATIONS

This application is a continuation of International Application No. PCT/JP2012/083356, filed on Dec. 21, 2012 which claims the benefit of priority of the prior Japanese Patent Application No. 2012-049781, filed on Mar. 6, 2012, the entire contents of which are incorporated herein by reference.

BACKGROUND OF THE INVENTION

1. Field of the Invention

The present invention relates to an endoscope system including an imaging apparatus that can output an electrical signal after photoelectric conversion, as image information, from pixels arbitrarily designated as a reading object among a plurality of pixels for imaging.

2. Description of the Related Art

In the related art, endoscope systems have been used to observe an organ of a subject such as a patient in medical fields. The endoscope system includes an insertion unit that has flexibility and an elongated shape, for example and is configured to be inserted into a body cavity of a subject, an imaging apparatus that is provided at a distal end of the insertion unit and is configured to capture an in-vivo image, and a display unit that can display the in-vivo image captured by the imaging apparatus. In order to acquire the in-vivo image by using the endoscope system, the insertion unit is inserted into the body cavity of the subject, and after that, living tissue in the body cavity is irradiated with irradiation light from the distal end of the insertion unit, and the imaging apparatus captures the in-vivo image. A user such as a doctor observes an organ of the subject based on the in-vivo image displayed on the display unit.

When imaging elements are incorporated into an imaging apparatus of the endoscope system for shipment, there is a need to correct pixel defect or characteristics of the imaging elements for shipment in order to correct variations inherent in the imaging elements. Correction information on contents performed in the correction is recorded in a management server or the like in association with identification information of the imaging elements.

As a technique of performing correction of imaging elements, disclosed is a technique where a chip integrated with recording elements where correction information is recorded and a chip integrated with imaging elements are installed in one package (refer to, for example, Japanese Laid-open Patent Publication No. 2007-208926). In this technique, the chip integrated with the recording elements where the correction information is recorded is installed in one package, and thus, the correction information is acquired from the recording elements at the time of correcting the imaging elements, so that the correction of the imaging elements is performed.

SUMMARY OF THE INVENTION

An endoscope system according to one aspect of the present invention includes an imaging apparatus that outputs, as image information, an electrical signal photoelectrically converted from a plurality of pixels, outside the imaging apparatus, and a processing apparatus that is connected to the imaging apparatus so as to bi-directionally communicate with the imaging apparatus. The imaging apparatus includes a first recording unit that records identification information for identifying the imaging apparatus. The processing apparatus includes a second recording unit that records correction information for correcting characteristics of the imaging apparatus in association with the identification information, and a control unit that acquires, from the second recording unit, the correction information corresponding to the identification information received from the imaging apparatus and transmits the correction information to the imaging apparatus. The control unit acquires the correction information recorded in the first recording unit, and if the acquired correction information is different from the correction information recorded in the second recording unit, the control unit transmits the correction information recorded in the second recording unit in association with the identification information to the imaging apparatus and causes the first recording unit to record the correction information recorded in the second recording unit, which is received from the control unit.

An endoscope system according to another aspect of the present invention includes an imaging apparatus that outputs, as image information, an electrical signal photoelectrically converted from a plurality of pixels, outside the imaging apparatus, a processing apparatus that is connected to the imaging apparatus so as to bi-directionally communicate with the imaging apparatus, and a management server that is connected to the processing apparatus so as to bi-directionally communicate with the processing apparatus. The imaging apparatus includes a first recording unit that records identification information for identifying the imaging apparatus. The processing apparatus includes a second recording unit that records correction information for correcting characteristics of the imaging apparatus in association with the identification information, and a control unit that acquires, from the second recording unit, the correction information corresponding to the identification information received from the imaging apparatus and transmits the correction information to the imaging apparatus. The management server includes: a database that records the correction information in association with the identification information; and a management controller that transmits the correction information, which is obtained by revising the correction information recorded in the second recording unit based on type information of an endoscope on which the imaging apparatus of the endoscope system is mounted, to the control unit if the correction information adjusted when the imaging apparatus corresponding to the identification information transmitted from the control unit is incorporated into the endoscope is different from the correction information recorded in the database. The control unit causes the first recording unit to record the correction information received from the management controller.

An endoscope system according to another aspect of the present invention includes an imaging apparatus that outputs, as image information, an electrical signal photoelectrically converted from a plurality of pixels, outside the imaging apparatus, a processing apparatus that is connected to the imaging apparatus so as to bi-directionally communicate with the imaging apparatus, and a management server that is connected to the processing apparatus so as to bi-directionally communicate with the processing apparatus. The imaging apparatus includes a first recording unit that records identification information for identifying the imaging apparatus. The processing apparatus includes a second recording unit that records correction information for correcting characteristics of the imaging apparatus in association with the identification information, and a control unit that acquires, from the second recording unit, the correction information corresponding to the identification information received from the imaging apparatus and transmits the correction information to the imaging apparatus. The management server includes: a database that records the correction information in association with the identification information; and a management controller that acquires inherent information of an endoscope on which the imaging apparatus of the endoscope system is mounted, specifies the imaging apparatus mounted on the endoscope system based on the acquired inherent information, and transmits the correction information, which is obtained by revising the correction information recorded in the first recording unit or the second recording unit based on the correction information for correcting the characteristics of the specified imaging apparatus, to the control unit if the correction information adjusted when the imaging apparatus corresponding to the identification information transmitted from the control unit is incorporated into the endoscope is different from the correction information recorded in the database. The control unit causes the first recording unit to record the correction information received from the management controller.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
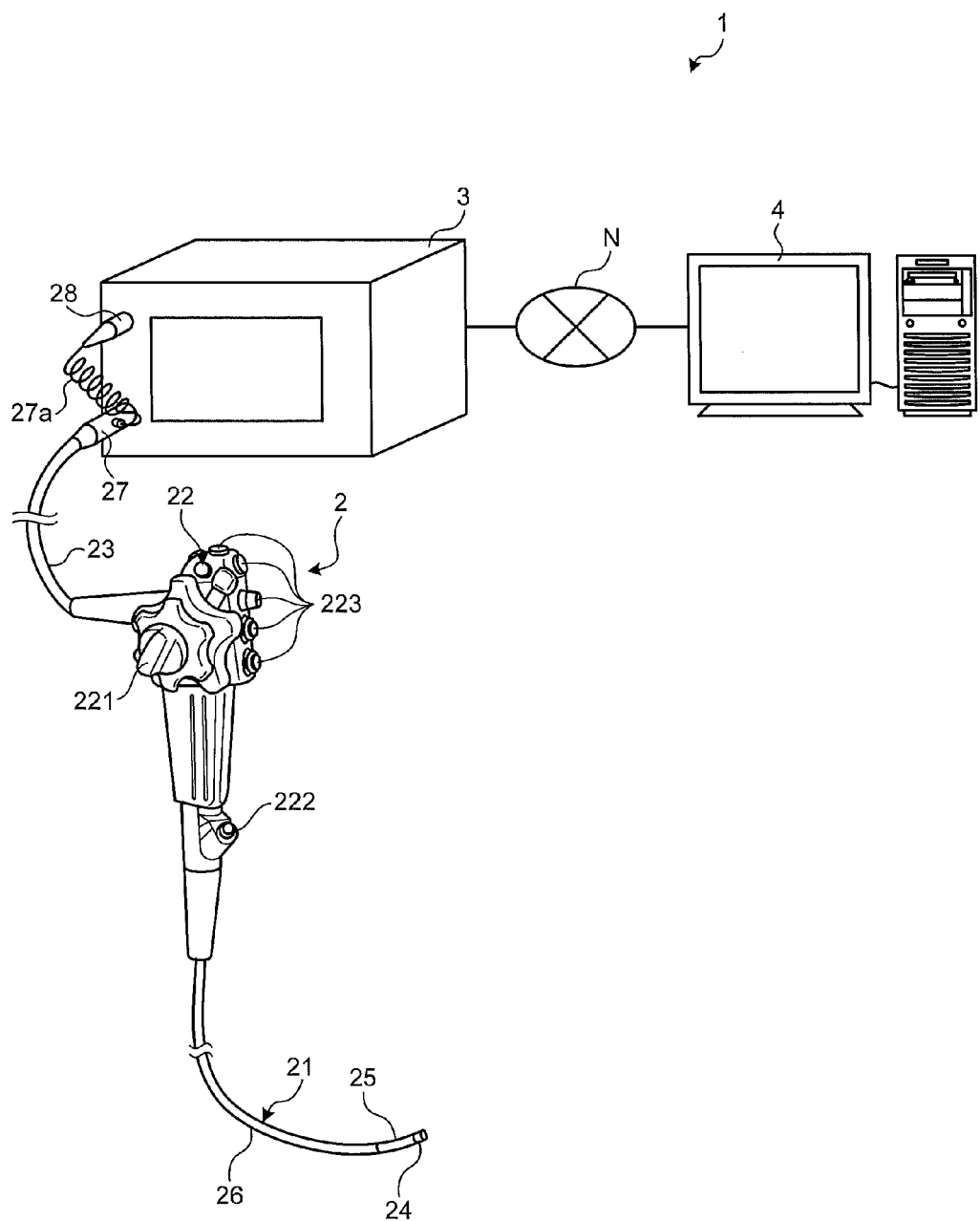
FIG. 1 is a schematic diagram illustrating a configuration of an endoscope system according to a first embodiment of the present invention.

Hereinafter, embodiments of a medical endoscope system which captures an internal image in a body cavity of a subject such as a patient will be described. The present invention is not limited to the embodiments. In the drawings, the same components are denoted by the same reference numerals.

First Embodiment

Figure 2:
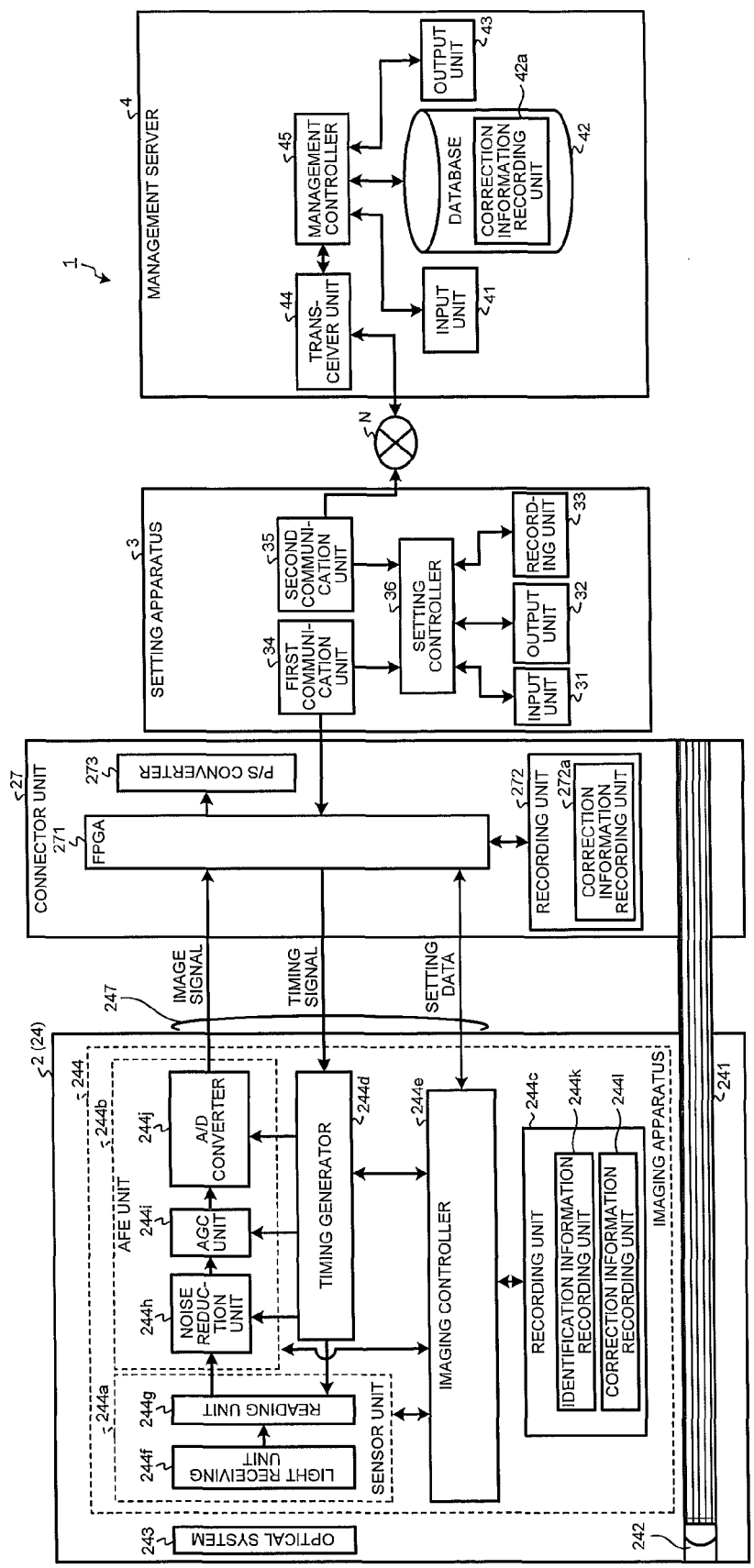
FIG. 2 is a block diagram illustrating a functional configuration of main components of the endoscope system according to the first embodiment of the present invention.

FIG. 1 is a schematic diagram illustrating a configuration of an endoscope system according to a first embodiment of the present invention. FIG. 2 is a block diagram illustrating a functional configuration of main components of the endoscope system according to the first embodiment of the present invention.

As illustrated in FIGS. 1 and 2, an endoscope system 1 includes an endoscope 2 (electronic scope) which inserts a distal end portion thereof into a body cavity of a subject and captures an in-vivo image of the subject, a setting apparatus 3 which performs various settings of the endoscope 2 before shipping the endoscope 2, and a management server 4 which records information on the endoscope 2. The setting apparatus 3 and the management server 4 are connected to each other through a network N so as to be able to communicate with each other.

The endoscope 2 includes an insertion unit 21 which is flexible and has an elongated shape, an operating unit 22 which is connected to a base end side of the insertion unit 21 and accepts an input of various manipulation signals, and a universal cord 23 which is extended in a direction different from the extension direction of the insertion unit 21 from the operating unit 22 and includes various cables connected to the setting apparatus 3.

The insertion unit 21 includes a distal end portion 24 which includes the below-described imaging apparatus, a bending portion 25 which is bendable and is configured with a plurality of bending pieces, and a flexible tube portion 26 which is connected to a base end side of the bending portion 25 and is formed with flexibility in an elongated shape.

The distal end portion 24 includes a light guide 241 which is configured by using a glass fiber or the like and constitutes a light path of light emitted by a light source apparatus (not illustrated), an illumination lens 242 provided at the distal end of the light guide 241, an optical system 243 for condensing light, and an imaging apparatus 244 which is provided at an image forming position of the optical system 243 to receive light condensed by the optical system 243, to photoelectrically convert the light into an electrical signal, to perform a specified signal process on the electrical signal, and to output the processed electrical signal outside the imaging apparatus 244.

The optical system 243 is configured by using one or a plurality of lenses and has an optical zooming function of changing an angle of view and a focusing function of changing focus.

The imaging apparatus 244 includes a sensor unit 244a which photoelectrically converts the light output from the optical system 243 to output an electrical signal, an analog front end 244b (hereinafter, referred to as an "AFE unit 244b") which performs signal processes such as noise reduction or A/D conversion on the electrical signal output from the sensor unit 244a, a recording unit 244c which records various types of information of the imaging apparatus 244, a timing generator 244d which generates driving timing of the sensor unit 244a and pulses for various signal processes in the AFE unit 244b, and an imaging controller 244e which controls operations of the imaging apparatus 244. The imaging apparatus 244 is a CMOS (complementary metal oxide semiconductor) image sensor (imaging element).

The AFE unit 244b includes a noise reduction unit 244h which reduces noise components included in an electrical signal (analog), an AGC (auto gain control) unit 244i which maintains a constant output level by adjusting amplification ratio (gain) of the electrical signal, and an A/D converter 244j which performs A/D conversion on the electrical signal as image information (image signal) output through the AGC unit 244i. The noise reduction unit 244h performs noise reduction by using, for example, a correlated double sampling method. The AFE unit 244b outputs the electrical signal (image signal) which is subject to the signal process to the below-described connector unit 27.

The recording unit 244c is configured by using a ROM, a Flash memory, or the like to record various kinds of information of the endoscope 2 and various programs executed by the imaging controller 244e. The recording unit 244c includes an identification information recording unit 244k which stores identification information (serial number or ID) for identifying the imaging apparatus 244 and a correction information recording unit 244l which records correction information on a light receiving unit 244f. Herein, the correction information includes pixel defect address information, color characteristic information, sensitivity variation information (including a variation of gain of a readout transistor), shading information, column (vertical line) variation information, type of pixel defect (for example, white or black scratches), a pixel correction method (for example, a method of performing two types of different corrections) and the like of the imaging apparatus 244. In addition, in the first embodiment, the recording unit 244c and/or a recording unit 272 function as a first recording unit.

The imaging controller 244e controls various operations of the distal end portion 24 according to the setting data received from the processing apparatus (not illustrated). The imaging controller 244e is configured by using a CPU (central processing unit) and the like.

The operating unit 22 includes a bending knob 221 which bends a bending portion 25 in up/down and left/right directions, a treatment tool insertion unit 222 which inserts a treatment tool such as a biological forceps, a laser scalpel, and a test probe into a body cavity, and a plurality of switches 223 as a manipulation input unit which inputs manipulation command signals for peripheral units such as an air supply unit, a water supply unit, and a gas supply unit in addition to the processing apparatus and the light source apparatus. The treatment tool inserted from the treatment tool insertion unit 222 is extracted from an opening (not illustrated) through a treatment tool channel (not illustrated) of the distal end portion 24.

The universal cord 23 includes at least a light guide 241 and a cable assembly 247 which combines one or a plurality of optical fibers. The universal cord 23 includes a connector unit 27 which is detachable to the setting apparatus 3. At the connector unit 27, a coil cable 27a having a coil shape is extendedly provided. At the extending end of the coil cable 27a, a connector unit 28 which is detachable to the processing apparatus is provided.

The connector unit 27 includes a field programmable gate array (FPGA) 271, a recording unit 272, and a P/S converter 273.

The FPGA 271 receives an electrical signal input from the imaging apparatus 244 and outputs the received electrical signal to the P/S converter 273.

The recording unit 272 is configured by using a ROM, a Flash memory, or the like to record various kinds of information of the endoscope 2 or various programs executed by the FPGA 271. The recording unit 272 includes a correction information recording unit 272a which records correction information on the imaging apparatus 244. The correction information corresponding to the identification information of the imaging apparatus 244 is recorded (stored) in the correction information recording unit 272a by the below-described setting apparatus 3.

The P/S converter 273 performs parallel-to-serial conversion on the electrical signal corresponding to the image information input from the FPGA 271 and outputs the converted electrical signal to an external processing apparatus (not illustrated).

Next, the configuration of the setting apparatus 3 will be described. The setting apparatus 3 is configured by using a personal computer and performs initial setting of the endoscope 2 before shipping the endoscope 2 or at the time of repairing the endoscope 2. Herein, the initial setting includes, for example, a recording process of recording correction information of the endoscope 2 before shipping the endoscope 2 or at the time of repairing the endoscope 2 and a calibration process for calibrating various data. The setting apparatus 3 includes an input unit 31, an output unit 32, a recording unit 33, a first communication unit 34, a second communication unit 35, and a setting controller 36. In addition, in the first embodiment, the setting apparatus 3 functions as a processing apparatus.

The input unit 31 is configured by using an input device such as a mouse or a keyboard, and accepts an input of various kinds of manipulation.

The output unit 32 is configured by using a liquid crystal device or an organic electro luminescence (EL) device. The output unit 32 outputs information on the setting apparatus 3 and information on the connected endoscope 2.

The recording unit 33 is configured by using a ROM, a Flash memory, or the like to record various kinds of information of the setting apparatus 3 and various programs executed by the setting apparatus 3.

The first communication unit 34 is a communication interface for performing communication with the endoscope 2 connected to the setting apparatus 3. The first communication unit 34 is connected to the connector unit 27 of the endoscope 2, so that bidirectional communication is performed. The first communication unit 34 outputs information transmitted from the endoscope 2 to the setting controller 36 and outputs information transmitted from the setting controller 36 to the endoscope 2.

The second communication unit 35 is a communication interface for performing communication with the management server 4 through the network N.

The setting controller 36 is configured by using a CPU and the like. The setting controller 36 transmits control signals or various data to each of the components constituting the setting apparatus 3 to collectively control the operations of the setting apparatus 3. The setting controller 36 acquires identification information of the endoscope 2 and acquires correction information corresponding to the acquired identification information from the management server 4 through the network N, and after that, the setting controller 36 records the correction information in the recording unit 244c of the endoscope 2 and/or the recording unit 272. In addition, in the first embodiment, the setting controller 36 functions as a control unit.

Next, the configuration of the management server 4 will be described. The management server 4 includes an input unit 41, a database 42, an output unit 43, a transceiver unit 44, and a management controller 45.

The input unit 41 is configured by using an input device such as a mouse or a keyboard, and accepts an input of various kinds of manipulation.

The database 42 includes a correction information recording unit 42a which records correction information corresponding to the identification information of each imaging apparatus 244. The correction information recording unit 42a records the correction information inherent in the imaging apparatus 244 on which an operator executes a correction process before shipping each imaging apparatus 244. The correction information is for correcting characteristics of the imaging apparatus 244. In addition, the correction information recording unit 42a may record correction information on the revision performed corresponding to the optical system to be installed in the endoscope and arrangement positions of the optical system at the time of assembling the endoscope. In addition, in the first embodiment, the database 42 functions as a second recording unit.

The transceiver unit 44 is a communication interface for performing communication with the setting apparatus 3 through the network N.

The management controller 45 is configured by using a CPU and the like. The management controller 45 transmits control signals or various data to each of the components constituting the management server 4 to collectively control the operations of the management server 4.

Figure 3:
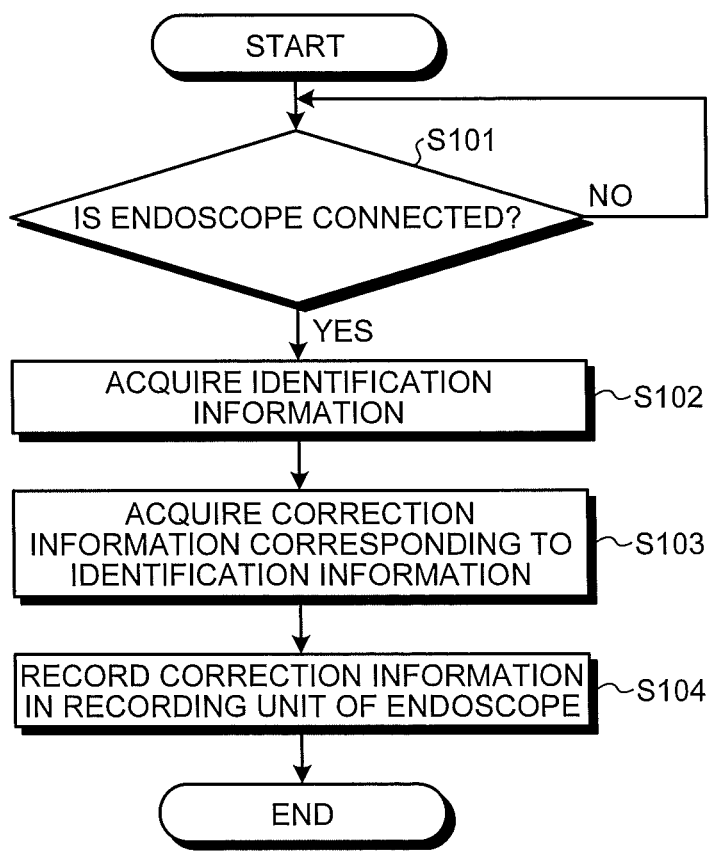
FIG. 3 is a schematic flowchart illustrating processes performed by a setting controller of the endoscope system according to the first embodiment of the present invention.

The process performed by the endoscope system 1 having the above-described configuration will be described. FIG. 3 is a schematic flowchart illustrating processes performed by the setting controller 36.

As illustrated in FIG. 3, the setting controller 36 determines whether or not the endoscope 2 is connected (Step S101). If the endoscope 2 is not connected (No in Step S101), the determination continues to be performed. On the contrary, if the endoscope 2 is connected (Yes in Step S101), the setting controller 36 proceeds to Step S102.

Subsequently, the setting controller 36 acquires identification information of the imaging apparatus 244 from the connected endoscope 2 (Step S102). More specifically, the setting controller 36 acquires the identification information of the imaging apparatus 244 from the identification information recording unit 244k of the recording unit 244c through the first communication unit 34 and the connector unit 27.

Next, the setting controller 36 acquires correction information corresponding to the acquired identification information from the management server 4 (Step S103). More specifically, the setting controller 36 communicates with the management server 4 through the second communication unit 35 and the network N to acquire correction information corresponding to the identification information from the correction information recording unit 42a of the database 42.

Subsequently, the setting controller 36 records the correction information acquired from the management server 4 in the recording unit of the endoscope 2 (Step S104). More specifically, the setting controller 36 records the correction information acquired from the management server 4 to the recording unit 244c of the imaging apparatus 244 and the recording unit 272 of the connector unit 27. In addition, the setting controller 36 may store only the correction information, for example, the pixel defect address in the recording unit 244c of the imaging apparatus 244 according to the type of the correction information. Next, the setting controller 36 ends the process.

According to the above-described first embodiment of the present invention, the setting controller 36 acquires correction information corresponding to the identification information of the imaging apparatus 244 acquired from the recording unit 244c of the imaging apparatus 244 from the management server 4 and records the acquired correction information in the recording unit 244c of the imaging apparatus 244 or the recording unit 272. Therefore, it is possible to securely records the correction information corresponding to the imaging apparatus 244 at the time of shipping or repairing the endoscope 2.

In addition, according to the first embodiment, since the identification information of the imaging apparatus 244 is allowed to be recorded in the recording unit 244c in the imaging apparatus 244 (in the imaging element), it is possible to securely prevent the identification information of the imaging apparatus 244 (serial number or ID information) from being lost.

In addition, according to the first embodiment, it is possible to collectively manage the correction information corresponding to the identification information of the imaging apparatus 244 by using the management server 4. In addition, it is possible to perform history management of the imaging apparatus 244 or the like.

Furthermore, according to the first embodiment, since the correction information corresponding to the imaging apparatus 244 can be securely recorded at the time of repairing of the endoscope 2, the operator does not record erroneous correction information.

In addition, according to the first embodiment, since the correction information required for correction of the light receiving unit 244f is allowed to be recorded in the recording unit 244c in the imaging apparatus 244 or the recording unit 272, it is possible to securely prevent correction from being performed by erroneously using correction information of a light receiving unit 244f of a different imaging apparatus.

In the first embodiment, the setting apparatus 3 is connected to the management server 4 through the network N. However, the database 42 may be provided in the setting apparatus 3.

Second Embodiment

Next, a second embodiment of the present invention will be described. The endoscope system according to the second embodiment can update or change correction information corresponding to the identification information of the imaging apparatus even after shipping of the endoscope. More specifically, the processing apparatus to which the endoscope is to be connected is connected to the management server, so that the endoscope system acquires the correction information to update or change the correction information. Therefore, hereinafter, after the endoscope system according to the second embodiment is described, the processes performed by the endoscope system according to the second embodiment will be described. The same components as those of the first embodiment are denoted by the same reference numerals in the description thereof.

Figure 4:
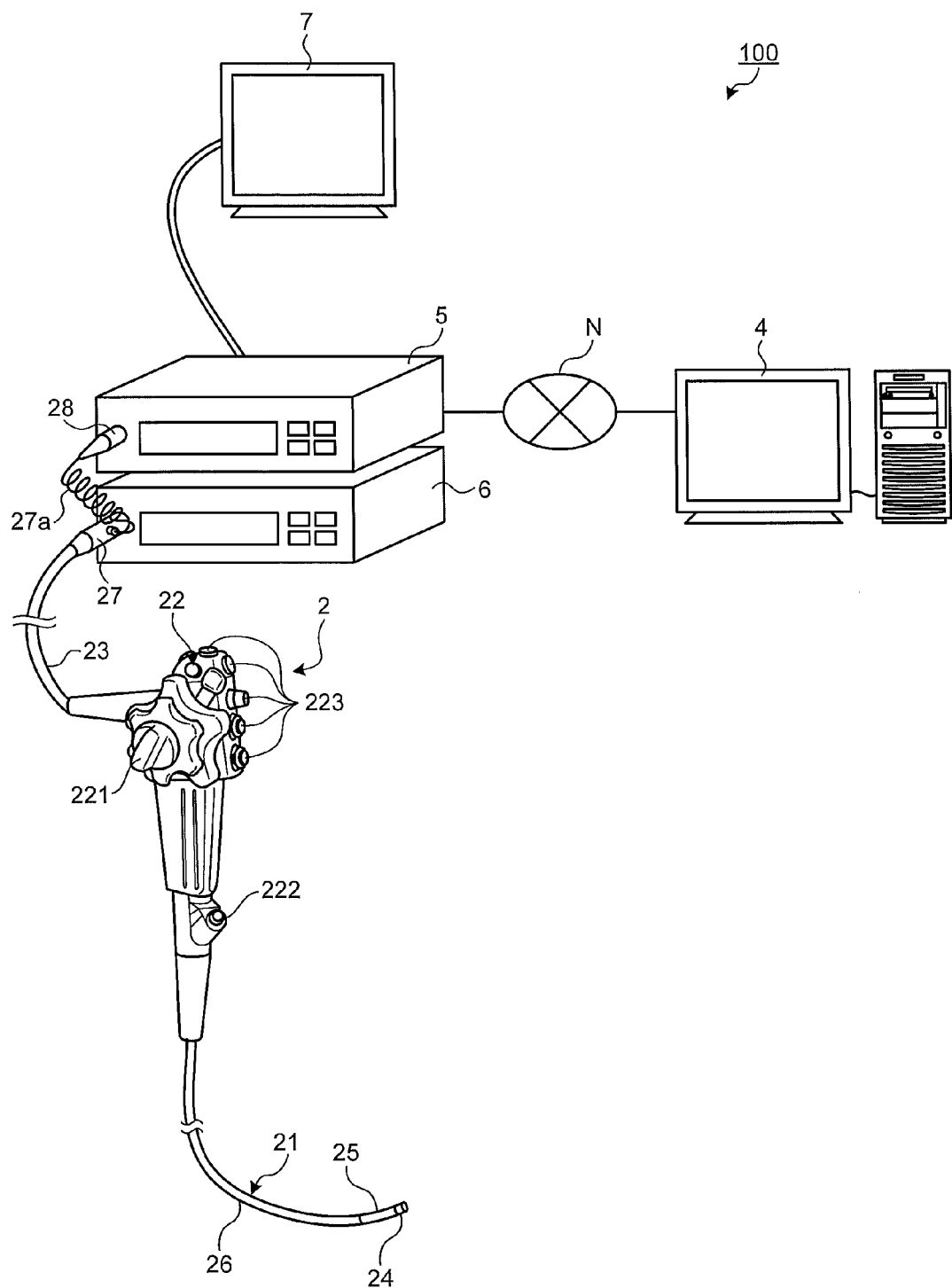
FIG. 4 is a schematic diagram illustrating a configuration of an endoscope system according to a second embodiment of the present invention.
Figure 5:
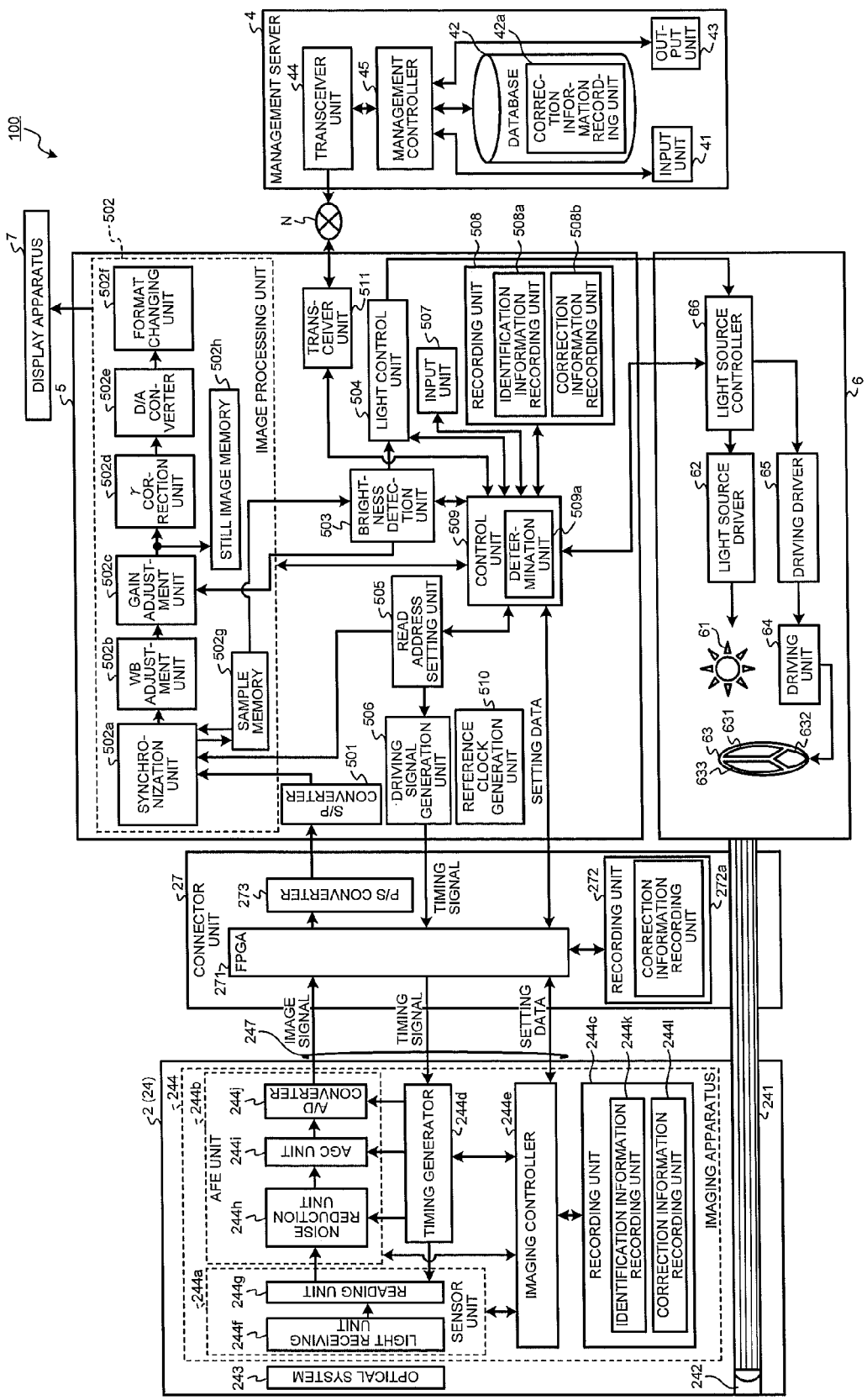
FIG. 5 is a block diagram illustrating a functional configuration of main components of the endoscope system according to the second embodiment of the present invention.

FIG. 4 is a schematic diagram illustrating a configuration of an endoscope system 100 according to the second embodiment. FIG. 5 is a block diagram illustrating a functional configuration of main components of the endoscope system 100 according to the second embodiment. As illustrated in FIGS. 4 and 5, the endoscope system 100 includes an endoscope 2, a processing apparatus 5 (external processor) which performs a specified image process on an in-vivo image captured by the endoscope 2 and collectively controls overall operations of the endoscope system 100, a light source apparatus 6 which generates irradiation light which is to be emitted from a distal end of the endoscope 2, a display apparatus 7 which displays the in-vivo image on which image process is performed by the processing apparatus 5, and a management server 4 which is connected to the processing apparatus 5 through a network N.

Next, the configuration of the processing apparatus 5 will be described. The processing apparatus 5 includes an S/P converter 501, an image processing unit 502, a brightness detection unit 503, a light control unit 504, a read address setting unit 505, a driving signal generation unit 506, an input unit 507, a recording unit 508, a control unit 509, a reference clock generation unit 510, and a transceiver unit 511.

The S/P converter 501 performs serial-to-parallel conversion on the image information (digital signal) of the electrical signal input from the P/S converter 273 of the connector unit 27 and outputs image information in a parallel format to the image processing unit 502.

The image processing unit 502 generates the in-vivo image which is to be displayed on the display apparatus 7 based on the image information in a parallel format input from the S/P converter 501. The image processing unit 502 includes a synchronization unit 502a, a white balance (WB) adjustment unit 502b, a gain adjustment unit 502c, a γ correction unit 502d, a D/A converter 502e, a format changing unit 502f, a sample memory 502g, and a still image memory 502h.

The synchronization unit 502a inputs the image information input as pixel information in three memories (not illustrated) provided for each pixel, sequentially updates and retains the values of the memories in association with the addresses of pixels of the light receiving unit 244f read by a reading unit 244g, and synchronizes the image information of the three memories as RGB image information. The synchronization unit 502a sequentially outputs the synchronized RGB image information to the white balance adjustment unit 502b and outputs some RGB image information as information for image analysis such as brightness detection to the sample memory 502g.

The white balance adjustment unit 502b automatically adjusts the white balance of the RGB image information. More specifically, the white balance adjustment unit 502b automatically adjusts the white balance of the RGB image information based on a color temperature included in the RGB image information.

The gain adjustment unit 502c adjusts a gain of the RGB image information. The gain adjustment unit 502c outputs the RGB signal of which gain is adjusted to the γ correction unit 502d and outputs some RGB signal as a signal for displaying a still image, a signal for displaying an enlarged image, or a signal for displaying an emphasized image to the still image memory 502h.

The γ correction unit 502d performs gradation correction (γ correction) of the RGB image information corresponding to the display apparatus 7.

The D/A converter 502e converts the RGB image information, of which gradation is corrected and which is output by the γ correction unit 502d, into an analog signal.

The format changing unit 502f converts the image information converted into an analog signal into a moving image file format such as a high vision format and outputs the converted image information to the display apparatus 7.

The brightness detection unit 503 detects a brightness level corresponding to each pixel from the RGB image information retained by the sample memory 502g to record the detected brightness level in a memory provided in the brightness detection unit 503 and to output the detected brightness level to the control unit 509. In addition, the brightness detection unit 503 calculates an adjusted gain value and an amount of irradiation light based on the detected brightness level to output the adjusted gain value to the gain adjustment unit 502c and to output the amount of irradiation light to the light control unit 504.

Under the control of the control unit 509, the light control unit 504 sets a type, amount, emitting timing, and the like of the light generated by the light source apparatus 6 based on the amount of irradiation light calculated by the brightness detection unit 503 and transmits a light source synchronizing signal including the setting conditions to the light source apparatus 6.

The read address setting unit 505 has a function of setting pixels as reading objects and a reading order on the light receiving plane of the sensor unit 244a. Namely, the read address setting unit 505 has a function of setting addresses of the pixels of the sensor unit 244a which are to be read by the AFE unit 244b. In addition, the read address setting unit 505 outputs the set address information of the pixels as reading objects to the synchronization unit 502a.

The driving signal generation unit 506 generates a driving timing signal for driving the imaging apparatus 244 and transmits the driving timing signal to the timing generator 244d through a specified signal line included in the cable assembly 247. The driving timing signal includes address information of the pixels as reading objects.

The input unit 507 accepts an input of various signals such as an operation command signal which commands an operation of the endoscope system 100.

The recording unit 508 is constructed by using a semiconductor memory such as a flash memory or a DRAM (dynamic random access memory). The recording unit 508 records various programs for operating the endoscope system 100 and data including various parameters and the like required for operations of the endoscope system 100. In addition, the recording unit 508 includes an identification information recording unit 508a which records identification information for identifying the endoscope 2 and a correction information recording unit 508b which records correction information used for correcting the imaging apparatus 244. Herein, the identification information includes information (ID) inherent in the processing apparatus 5, model year of the processing apparatus 5, specification information of the control unit 509, a transmission method, a transmission rate, and the like.

The control unit 509 is configured by using a CPU and the like. The control unit 509 performs driving control of components including the distal end portion 24 and the light source apparatus 6 and performs input and output control of information for the components. The control unit 509 transmits the setting data for imaging control to the imaging controller 244e through a specified signal line included in the cable assembly 247.

The reference clock generation unit 510 generates a reference clock signal as a reference of operations of the components of the endoscope system 100 and supplies the generated reference clock signal to the components of the endoscope system 100.

Next, the configuration of the light source apparatus 6 will be described. The light source apparatus 6 includes a light source 61, a light source driver 62, a rotation filter 63, a driving unit 64, a driving driver 65, and a light source controller 66.

The light source 61 is configured by using a white LED to generate white light under the control of the light source controller 66. The light source driver 62 supplies current to the light source 61 under the control of the light source controller 66 to allow the light source 61 to generate the white light. The light generated by the light source 61 is irradiated through the rotation filter 63, a condenser lens (not illustrated), and the light guide 241 from the distal end of the distal end portion 24. In addition, the light source 61 may be configured by using a xenon lamp or the like.

The rotation filter 63 is disposed on an optical path of white light emitted by the light source 61 to rotate, so that the rotation filter 63 passes only the light having a specified wavelength band among the white light emitted by the light source 61. More specifically, the rotation filter 63 includes a red filter 631, a green filter 632, and a blue filter 633 which pass light having corresponding wavelength bands of red light (R), green light (G), and blue light (B). The rotation filter 63 is rotated to sequentially pass light having red, green, and blue wavelength bands (for example, red: 600 nm to 700 nm, green: 500 nm to 600 nm, and blue: 400 nm to 500 nm). Therefore, from the white light emitted by the light source 61, red light, green light, and blue light in narrow bands can be sequentially emitted to the endoscope 2.

The driving unit 64 is configured by using a step motor, a DC motor, or the like to allow the rotation filter 63 to be rotated. The driving driver 65 supplies a specified current to the driving unit 64 under the control of the light source controller 66.

The light source controller 66 controls an amount of current supplied to the light source 61 according to the light source synchronizing signal transmitted from the light control unit 504. In addition, the light source controller 66 allows the driving unit 64 to drive through the driving driver 65 under the control of the control unit 509, so that the rotation filter 63 is rotated.

The display apparatus 7 has a function of receiving the in-vivo image generated by the processing apparatus 5 from the processing apparatus 5 through a video cable and displaying the in-vivo image. The display apparatus 7 is configured by using a liquid crystal device or an organic EL device.

Figure 6:
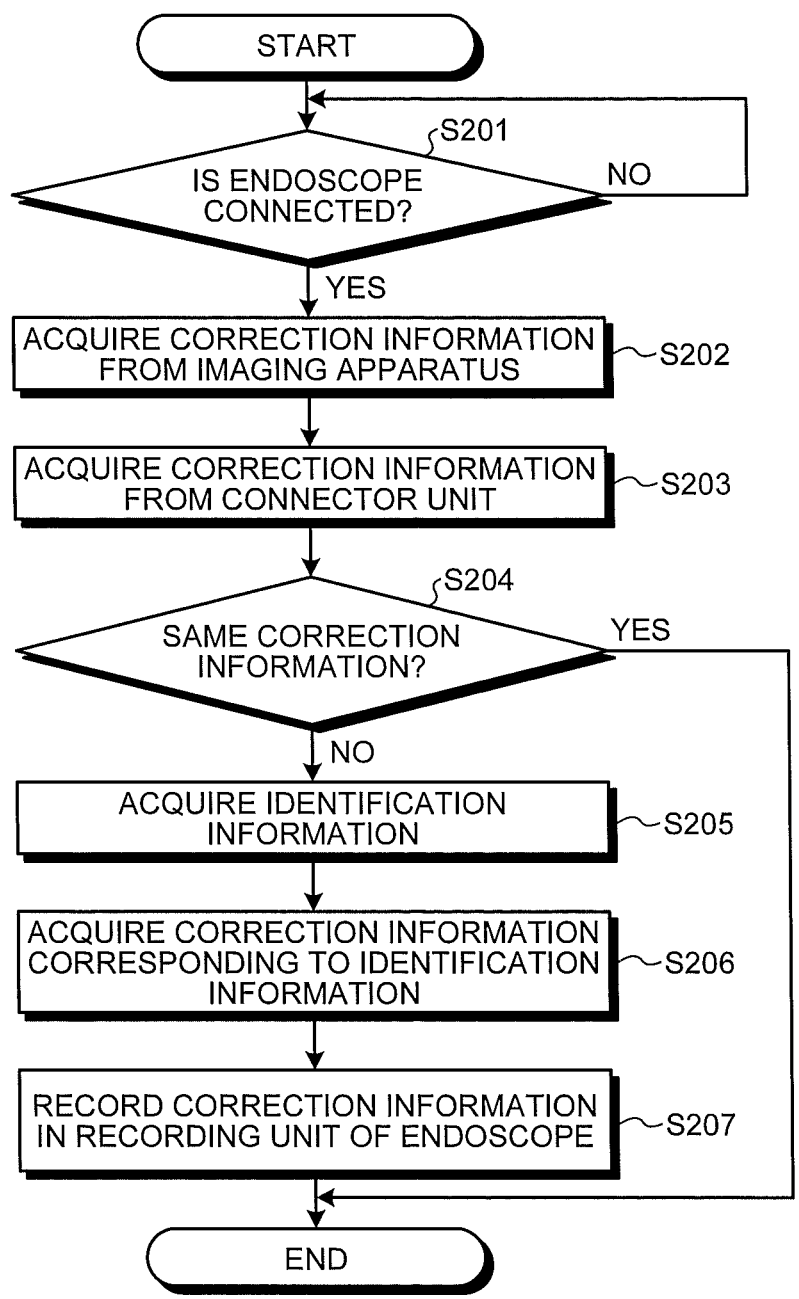
FIG. 6 is a schematic flowchart illustrating processes performed by the endoscope system according to the second embodiment of the present invention.

Processes performed by the endoscope system 100 having the above-described configuration will be described. FIG. 6 is a schematic flowchart illustrating processes performed by the endoscope system 100.

As illustrated in FIG. 6, the control unit 509 determines whether or not the endoscope 2 is connected to the processing apparatus 5 (Step S201). If the control unit 509 determines that the endoscope 2 is not connected to the processing apparatus 5 (No in Step S201), the determination continues to be performed. On the contrary, if the control unit 509 determines that the endoscope 2 is connected to the processing apparatus 5 (Yes in Step S201), the endoscope system 100 proceeds to Step S202.

Subsequently, the control unit 509 acquires the correction information from the correction information recording unit 244*l* of the recording unit 244*c* of the imaging apparatus 244 (Step S202) and acquires correction information from the correction information recording unit 272*a* of the recording unit 272 of the connector unit 27 (Step S203).

Next, a determination unit 509*a* determines whether or not the correction information recorded in the recording unit 244*c* and the correction information recorded in the recording unit 272 are equal to data of the correction information acquired from the correction information recording unit 42*a* of the database 42 of the management server 4 through the network N, by comparison (Step S204). In addition, the determination unit 509*a* may determine whether or not the correction information acquired from the imaging apparatus 244 and the correction information acquired from the connector unit 27 are equal to each other. For example, the determination unit 509*a* may determine whether or not the pixel defect address of the light receiving unit 244*f* included in the correction information acquired from the imaging apparatus 244 and the pixel defect address of the light receiving unit 244*f* included in the correction information acquired from the connector unit 27 are equal to each other. If the determination unit 509*a* determines that the correction information acquired from the imaging apparatus 244 and the correction information acquired from the connector unit 27 are equal to the correction information recorded in the database 42 of the management server 4 (Yes in Step S204), the endoscope system 100 ends the process. On the contrary, if the determination unit 509*a* determines that the correction information acquired from the imaging apparatus 244 and the correction information acquired from the connector unit 27 are not equal to the correction information recorded in the database 42 of the management server 4 (No in Step S204), the endoscope system 100 proceeds to Step S205.

Subsequently, the control unit 509 acquires identification information from the identification information recording unit 244*k* in the recording unit 244*c* of the imaging apparatus 244 (Step S205) and acquires correction information corresponding to the acquired identification information from the correction information recording unit 42*a* of the database 42 of the management server 4 through the network N (Step S206). At this time, if the correction information corresponding to the identification information is recorded in the correction information recording unit 508*b* of the recording unit 508, the control unit 509 may not acquire the correction information from the management server 4.

Next, the control unit 509 records the correction information acquired from the management server 4 in the recording unit 244*c* of the endoscope and the recording unit 272 (Step S207). At this time, the control unit 509 may record only the pixel defect address information of the light receiving unit 244*f* included in the correction information acquired from the management server 4 in the correction information recording unit 244*l* of the recording unit 244*c*. Accordingly, since the capacity of the recording unit 244*c* can be reduced, it is possible to decrease the diameter of the distal end portion 24. In addition, with respect to the correction information of which characteristics are not changed after shipping, since it is unnecessary to update the correction information in the recording unit 244*c*, only the information in the recording unit 272 may be updated. After Step S207, the endoscope system 100 ends the process.

According to the above-described second embodiment of the present invention, the control unit 509 acquires correction information corresponding to the identification information of the imaging apparatus 244 acquired from the recording unit 244*c* of the imaging apparatus 244 from the management server 4 and records the acquired correction information in the recording unit 244*c* of the imaging apparatus 244. Therefore, at the time of testing a subject, it is possible to securely perform testing the subject by using the correction information corresponding to the imaging apparatus 244 without using erroneous correction information.

In addition, according to the second embodiment, since the identification information of the imaging apparatus 244 is allowed to be recorded in the recording unit 244*c* in the imaging apparatus 244, it is possible to securely prevent the identification information of the imaging apparatus 244 (serial number or ID information) from being lost.

In addition, according to the second embodiment, the control unit 509 compares the correction information recorded by the recording unit 244*c* of the imaging apparatus 244 and the correction information recorded by the recording unit 272 of the connector unit 27 to the correction information recorded in the database 42 of the management server 4. At this time, if the data of the correction information are different, the control unit 509 acquires the correction information corresponding to the identification information of the imaging apparatus 244 from the management server 4 to record the correction information in the recording unit 244*c* and the recording unit 272. Therefore, even if the imaging apparatus 244 in the endoscope 2 is replaced with a different imaging apparatus 244 at the time of repairing, it is possible to test the subject without using erroneous correction information.

In addition, in the second embodiment, the control unit 509 records the correction information corresponding to the identification information of the imaging apparatus 244 acquired from the management server 4 in the recording unit 244c of the imaging apparatus 244 of the endoscope 2 and recording unit 272 of the connector unit 27. However, the control unit 509 may also record the correction information in the recording unit 508 of the processing apparatus 5. In this case, the control unit 509 may record only correction information, for example, color characteristic information and shading information needed for an image signal generated by the imaging apparatus 244 in the recording unit 508. In addition, the control unit 509 may also record all the correction information corresponding to the imaging apparatus 244 acquired from the management server 4 in the recording unit 508.

In addition, in the second embodiment, the imaging apparatus 244 may be configured to transmit the identification information or the correction information recorded in the recording unit 244c to the processing apparatus 5 or the recording unit 272 at the time of starting up the endoscope system 100. In addition, the identification information and the correction information of the imaging apparatus 244 may be superimposed on the image signal to be periodically transmitted to the processing apparatus 5. At this time, the identification information and the correction information may be transmitted during the blanking period of the image signal.

Modified Example 1 of Second Embodiment

Figure 7:
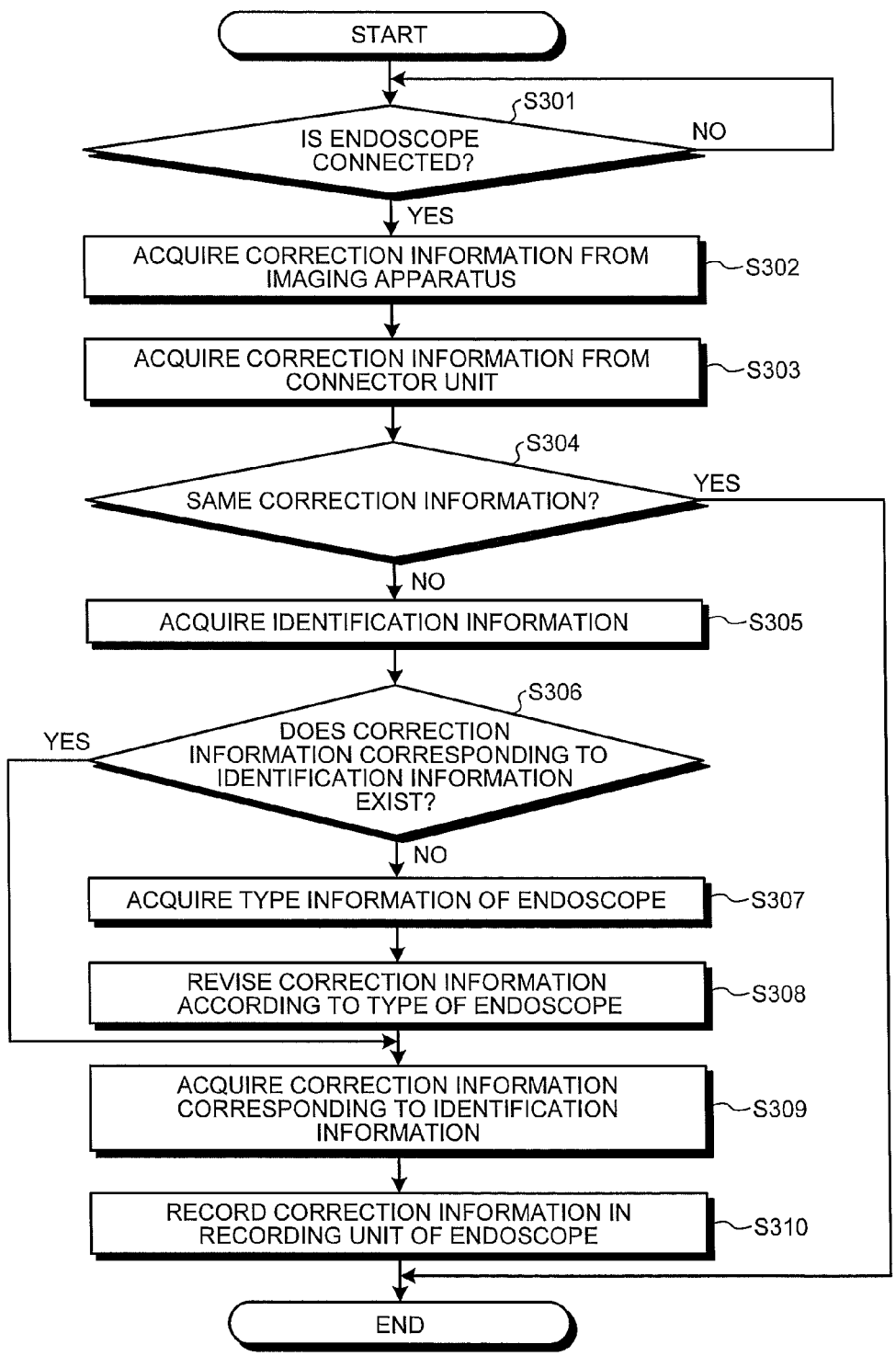
FIG. 7 is a schematic flowchart illustrating processes performed by an endoscope system according to Modified Example 1 of the second embodiment of the present invention.

FIG. 7 is a schematic flowchart illustrating processes performed by an endoscope system according to Modified Example 1 of the second embodiment. The same components as those of the above-described second embodiment are denoted by the same reference numerals in the description thereof.

Steps S301 to S305 correspond to Steps S201 to S205 of FIG. 6, respectively.

In Step S306, the management controller 45 of the management server 4 determines whether or not the correction information adjusted at the time of incorporating the imaging apparatus 244 corresponding to the identification information transmitted from the control unit 509 into the endoscope 2 is recorded in the correction information recording unit 42a (Step S306). If the management controller 45 of the management server 4 determines that the correction information adjusted at the time of incorporating the correction information of the imaging apparatus 244 corresponding to the identification information into the endoscope 2 is recorded in the correction information recording unit 42a (Yes in Step S306), the endoscope system 100 proceeds to the below-described Step S309. On the contrary, if the management controller 45 of the management server 4 determines that the correction information adjusted at the time of incorporating the correction information of the imaging apparatus 244 corresponding to the identification information into the endoscope 2 is not recorded in the correction information recording unit 42a (No in Step S306), the endoscope system 100 proceeds to the below-described Step S307.

In Step S307, the management controller 45 of the management server 4 acquires type information of the endoscope 2 from the recording unit 272 of the connector unit 27 through the control unit 509.

Subsequently, the management controller 45 of the management server 4 revises the correction information inherent in the imaging apparatus 244 according to the type information of the endoscope 2 (Step S308). The management controller 45 of the management server 4 transmits the revised correction information to the control unit 509, and the control unit 509 records the correction information revised in the below-described Step S309 in the recording unit 244c of the endoscope 2 or the recording unit 272.

Steps S309 and S310 correspond to Steps S206 and S207 of FIG. 6, respectively. After Step S310, the endoscope system 100 ends the process.

According to Modified Example 1 of the second embodiment of the invention described hereinbefore, although the imaging apparatus 244 (imaging element) is replaced due to the repairing, the correction information corresponding to the endoscope 2 can be acquired.

Modified Example 2 of Second Embodiment

Figure 8:
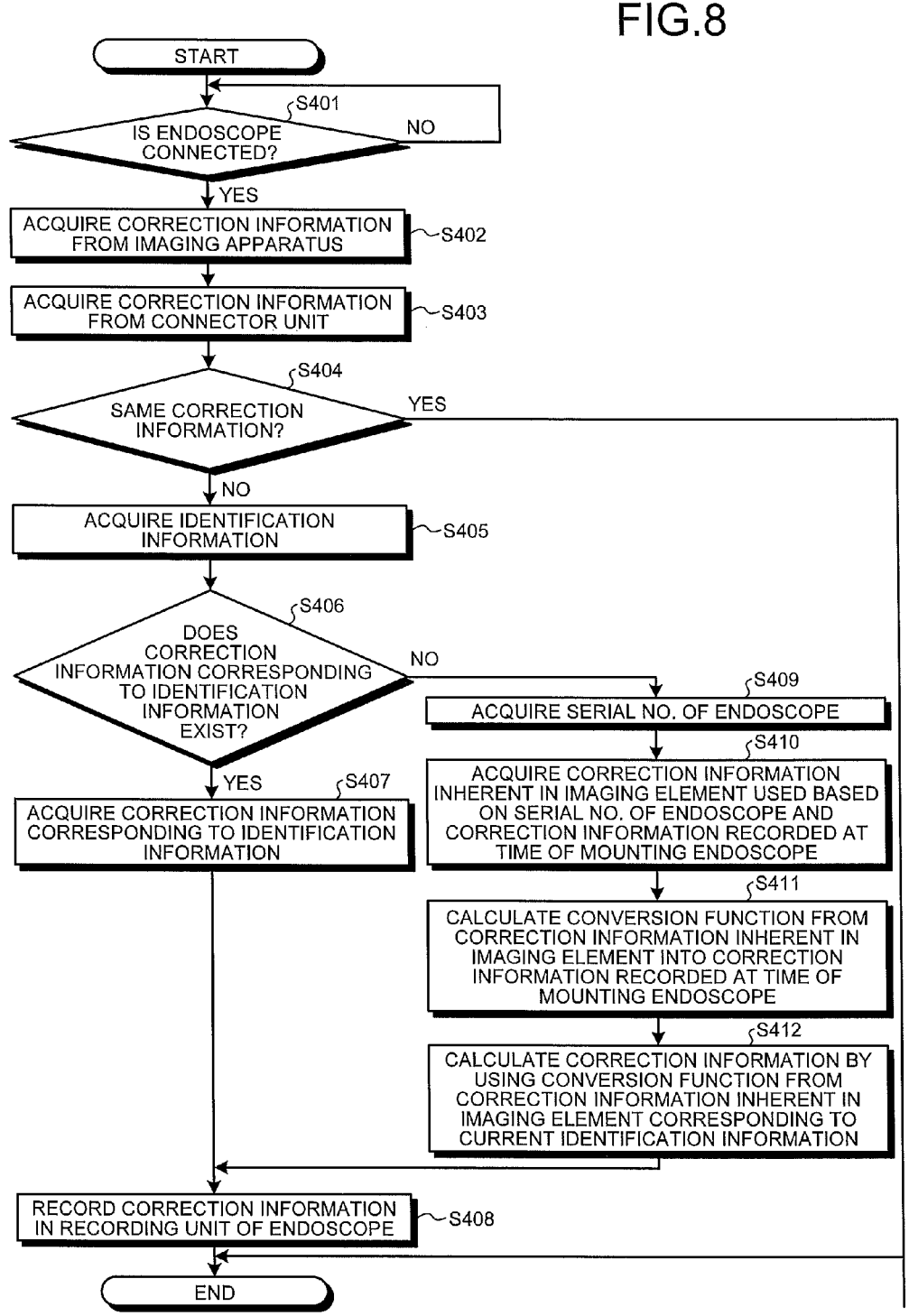
FIG. 8 is a schematic flowchart illustrating processes performed by an endoscope system according to Modified Example 2 of the second embodiment of the present invention.

FIG. 8 is a schematic flowchart illustrating processes performed by an endoscope system according to Modified Example 2 of the second embodiment. The same components as those of the above-described second embodiment are denoted by the same reference numerals in the description thereof.

Steps S401 to S405 correspond to Steps S201 to S205 of FIG. 6, respectively.

In Step S406, the management controller 45 of the management server 4 determines whether or not the correction information adjusted at the time of incorporating the imaging apparatus 244 corresponding to the identification information transmitted from the control unit 509 into the endoscope is recorded in the correction information recording unit 42a (Step S406). If the management controller 45 of the management server 4 determines that the correction information adjusted at the time of incorporating the correction information of the imaging apparatus 244 corresponding to the identification information into the endoscope is recorded in the correction information recording unit 42a (Yes in Step S406), the endoscope system 100 proceeds to the below-described Step S407. On the contrary, if the management controller 45 of the management server 4 determines that the correction information adjusted at the time of incorporating the correction information of the imaging apparatus 244 corresponding to the identification information into the endoscope is not recorded in the correction information recording unit 42a (No in Step S406), the endoscope system 100 proceeds to the below-described Step S409.

Steps S407 and S408 correspond to Steps S206 and S207 of FIG. 6, respectively. After Step S408, the endoscope system 100 ends the process.

In Step S409, the management controller 45 of the management server 4 acquires the serial number of the endoscope 2 from the recording unit 272 through the control unit 509.

Subsequently, the management controller 45 of the management server 4 acquires the correction information inherent in the imaging apparatus 244 (inherent in the imaging element) used based on the serial number of the endoscope 2 and acquires the correction information recorded at the time of mounting the endoscope 2 from the correction information recording unit 508b of the recording unit 508 or the correction information recording unit 42a of the management server 4 through the control unit 509 (Step S410).

Next, the management controller 45 of the management server 4 calculates a conversion function for the correction information inherent in the imaging apparatus 244 (inherent in the imaging element) into the correction information recorded at the time of mounting the endoscope 2 based on the acquired correction information inherent in the imaging apparatus 244 (inherent in the imaging element) and the acquired correction information recorded at the time of mounting the endoscope 2 (Step S411).

Subsequently, the management controller 45 of the management server 4 calculates the correction information from the correction information, which is recorded in the correction information recording unit 42a and is inherent in the imaging apparatus 244 (inherent in the imaging element) corresponding to the current identification information which is recorded in the identification information recording unit 244k, by using the conversion function (Step S412). Next, the endoscope system 100 proceeds to Step S408, where the management controller 45 of the management server 4 transmits the converted correction information to the control unit 509, and the control unit 509 records the correction information calculated by using the conversion function in the recording unit 244c of the endoscope 2 or the recording unit 272.

According to Modified Example 2 of the second embodiment of the invention described hereinbefore, although the imaging apparatus 244 (imaging element) is replaced due to the repairing, the correction information corresponding to the endoscope 2 can be acquired, and information corresponding to individual differences of the endoscopes 2 can also be included in the correction information after the replacement. In addition, information on the used imaging apparatus 244 (imaging element) is recorded in the recording unit 272, and the correction information inherent in the imaging apparatus 244 (inherent in the imaging element) may be acquired by using the information.

Other Embodiments

In the embodiment, although the correction information corresponding to the identification information of the imaging apparatus 244 is recorded in the recording unit 272 of the connector unit 27, a recording unit may be provided in the operating unit 22 so that the correction information is recorded in the recording unit.

In addition, in the embodiment, the imaging controller 244e may automatically correct the pixel defect of the sensor unit 244a. In this case, the imaging controller 244e compares data of each pixel of the sensor unit 244a to an average value of the data of eight or more peripheral pixels, detects the pixel corresponding to the data of which value is lower than the average value as pixel defect, and records the address of the detected pixel defect in the recording unit 244c. In addition, since there is a possibility that the pixel defect occurs in the peripheral pixels, the imaging controller 244e may perform the above comparison pixel by pixel. Accordingly, it is possible to output an image having no sense of strangeness. In addition, even if the imaging apparatus 244 is replaced at the time of repairing, there is no need to perform address setting for the pixel defect. Furthermore, since the imaging apparatus 244 itself corrects the defective pixel, an image signal having no white or black scratches can be output.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
an imaging apparatus that outputs, as image information, an electrical signal photoelectrically converted from a plurality of pixels, outside the imaging apparatus; and
a processing apparatus that is connected to the imaging apparatus so as to bi-directionally communicate with the imaging apparatus,
wherein the imaging apparatus includes a first recording unit that records identification information for identifying the imaging apparatus,
wherein the processing apparatus includes:
a second recording unit that records correction information for correcting characteristics of the imaging apparatus in association with the identification information; and
a control unit that acquires, from the second recording unit, the correction information corresponding to the identification information received from the imaging apparatus and transmits the correction information to the imaging apparatus, and
wherein the control unit acquires the correction information recorded in the first recording unit, and if the acquired correction information is different from the correction information recorded in the second recording unit, the control unit transmits the correction information recorded in the second recording unit in association with the identification information to the imaging apparatus and causes the first recording unit to record the correction information recorded in the second recording unit, which is received from the control unit.

2. An endoscope system comprising:
an imaging apparatus that outputs, as image information, an electrical signal photoelectrically converted from a plurality of pixels, outside the imaging apparatus;
a processing apparatus that is connected to the imaging apparatus so as to bi-directionally communicate with the imaging apparatus; and
a management server that is connected to the processing apparatus so as to bi-directionally communicate with the processing apparatus,
wherein the imaging apparatus includes a first recording unit that records identification information for identifying the imaging apparatus,
wherein the processing apparatus includes:
a second recording unit that records correction information for correcting characteristics of the imaging apparatus in association with the identification information; and
a control unit that acquires, from the second recording unit, the correction information corresponding to the identification information received from the imaging apparatus and transmits the correction information to the imaging apparatus, and
wherein the management server includes:
a database that records the correction information in association with the identification information; and
a management controller that transmits the correction information, which is obtained by revising the correction information recorded in the second recording unit based on type information of an endoscope on which the imaging apparatus of the endoscope system is mounted, to the control unit if the correction information adjusted when the imaging apparatus corresponding to the identification information transmitted from the control unit is incorporated into the endoscope is different from the correction information recorded in the database, and
wherein the control unit causes the first recording unit to record the correction information received from the management controller.

3. An endoscope system comprising:
an imaging apparatus that outputs, as image information, an electrical signal photoelectrically converted from a plurality of pixels, outside the imaging apparatus;

a processing apparatus that is connected to the imaging apparatus so as to bi-directionally communicate with the imaging apparatus; and a management server that is connected to the processing apparatus so as to bi-directionally communicate with the processing apparatus, wherein the imaging apparatus includes a first recording unit that records identification information for identifying the imaging apparatus, wherein the processing apparatus includes:

a second recording unit that records correction information for correcting characteristics of the imaging apparatus in association with the identification information; and a control unit that acquires, from the second recording unit, the correction information corresponding to the identification information received from the imaging apparatus and transmits the correction information to the imaging apparatus, and wherein the management server includes:

a database that records the correction information in association with the identification information; and a management controller that acquires inherent information of an endoscope on which the imaging apparatus of the endoscope system is mounted, specifies the imaging apparatus mounted on the endoscope system based on the acquired inherent information, and transmits the correction information, which is obtained by revising the correction information recorded in the first recording unit or the second recording unit based on the correction information for correcting the characteristics of the specified imaging apparatus, to the control unit if the correction information adjusted when the imaging apparatus corresponding to the identification information transmitted from the control unit is incorporated into the endoscope is different from the correction information recorded in the database, and wherein the control unit causes the first recording unit to record the correction information received from the management controller.

* * * * *